US 6,616,673 B1

(12) United States Patent
Stone et al.

(10) Patent No.: US 6,616,673 B1
(45) Date of Patent: Sep. 9, 2003

(54) SEGMENTED JOINT DISTRACTOR

(75) Inventors: Kevin Thomas Stone, Winona Lake, IN (US); Ryan Cameron Lakin, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 0 days.

(21) Appl. No.: 09/838,456

(22) Filed: Apr. 19, 2001

(51) Int. Cl.⁷ .............................................. A61B 17/66
(52) U.S. Cl. ...................................................... 606/105
(58) Field of Search ................................ 606/105, 191, 606/192, 198; 623/17.12; 604/101.01, 919

(56) References Cited

U.S. PATENT DOCUMENTS

| | | |
|---|---|---|
| 4,299,227 A | 11/1981 | Lincoff |
| 4,312,353 A | 1/1982 | Shahbabian |
| 5,019,042 A * | 5/1991 | Sahota .................. 604/101.01 |
| 5,163,949 A | 11/1992 | Bonutti |
| 5,176,683 A | 1/1993 | Kimsey et al. |
| 5,308,327 A | 5/1994 | Heaven et al. |
| 5,331,975 A | 7/1994 | Bonutti |
| 5,620,457 A * | 4/1997 | Pinchasik et al. ............ 606/194 |
| 5,782,740 A * | 7/1998 | Schneiderman ................. 600/1 |
| 5,820,595 A * | 10/1998 | Parodi .................... 604/101.05 |
| 5,910,101 A * | 6/1999 | Andrews et al. ................ 600/3 |
| 5,972,015 A | 10/1999 | Scribner et al. |
| 5,984,943 A | 11/1999 | Young |
| 6,015,421 A | 1/2000 | Echeverry et al. |
| 6,017,305 A | 1/2000 | Bonutti |
| 6,048,346 A | 4/2000 | Reiley et al. |
| 6,235,043 B1 * | 5/2001 | Reiley et al. ................ 606/192 |

* cited by examiner

Primary Examiner—Kevin Shaver
Assistant Examiner—Michael B. Priddy
(74) Attorney, Agent, or Firm—Harness, Dickey & Pierce, P.L.C.

(57) ABSTRACT

A joint distraction device for facilitating joint arthroscopy disclosed. In the first embodiment of the invention, the distractor disclosed is a series of fluidly fillable spheroid members to form a toroid. The joint distractor is placed between articular cartilage surfaces and filled to hold the joint surfaces apart. In a second embodiment of the invention, a string of spheroidal members is disclosed. The spheroidal members have varying diameters and are used to separate the articular surfaces of a joint.

12 Claims, 4 Drawing Sheets

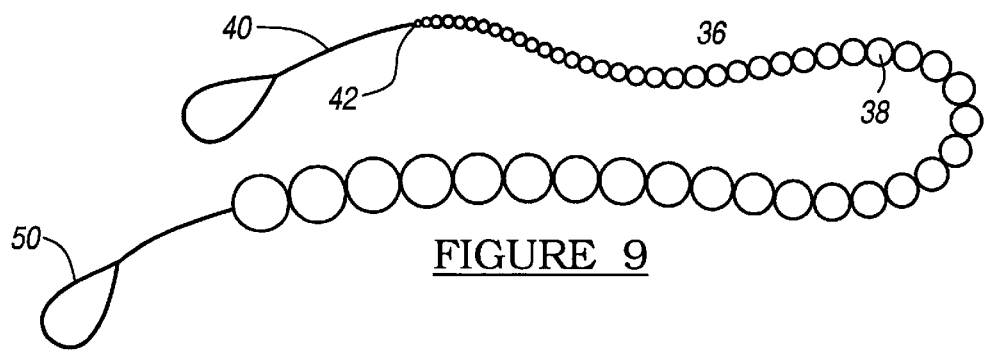
FIGURE 9
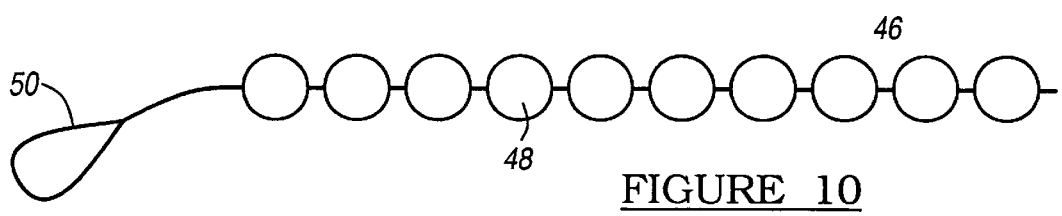
FIGURE 10
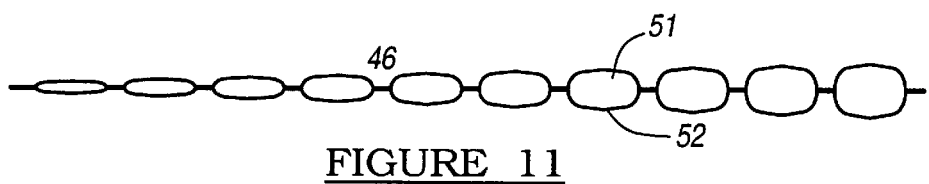
FIGURE 11
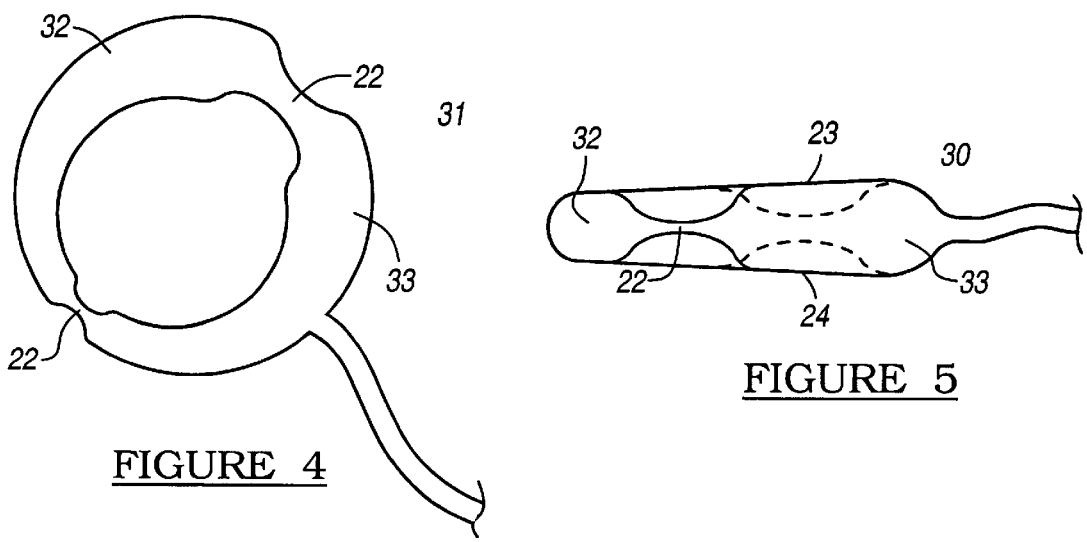
FIGURE 4
FIGURE 5

SEGMENTED JOINT DISTRACTOR

BACKGROUND OF THE INVENTION

1. Technical Field

This invention generally relates to an orthopedic instrument used to distract a joint, and more particularly, to a segmented joint distractor which allows for access into a distracted joint.

2. Discussion

Joint arthroscopy is a relatively young treatment modality for treating painful joints. Its primary function is to diagnose joint pathology. Additionally, debridement, joint flushing and smoothing of the joint surfaces has led to reduced pain and a return to more normal activities.

An important step in arthroscopy is to assure that not only are the bones of the joint properly aligned, but also that both joint surfaces are accessible. Failure of both joint surfaces being accessible can lead to significant trauma to the surrounding joint soft tissue, which leads to significant recovery time.

The joint surfaces are spanned by muscles, ligaments or other soft tissue. For example, in the knee joint, the collateral ligaments are both equally tight in the joint. This tension in the collateral ligaments prevents sideways toggle of the appendage. The ACL and PCL limit the amount of anterior and posterior motion in the knee joint. These ligaments limit the amount the joint can be separated to create access to the joint surfaces.

The knee is a superficial joint because there is little soft tissue between the skin and the joint as compared to the hip. Access is achieved by a combination of flexion and extension to give the clinician direct view of the various anatomic structures. At times, hand distraction and rotation can be used to increase exposure.

While the current invention has more application in total joint surgery where ligament balancing is key, it has uses in other surgical procedures. In another example, gaining access to the bearing surfaces of a hip joint with minimal tissue disruption is often complex and relatively ineffective. Current methods, for example, to perform hip arthroscopy utilize elongated arthroscopy instruments to obtain access to the joint which lies under many thick layers of muscle and soft tissue. Distraction normally is applied to the leg to create approximately 5 to 7 millimeters of joint displacement. Access to limited portions of the intra-articular area can then be achieved.

This distraction of the joint applies force to the patient's foot and a counterforce to the patient's groin area. This mode of distraction is only marginally effective. Possible side effects to this surgery include numbness, nerve damage, and impotence. Additionally, the immobilized leg is not free to be manipulated to allow visualization of the articular cartilage areas.

Other apparatus attempt to separate various inner body regions by use of a fluid operated regulator. Typically, a balloon is positioned at the desired location within the body for developing an atomic space at the desired location. The apparatus typically includes a tunneling member and an inflatable balloon. The tunneling member has a substantially rigid tubular shaft with proximal and distal ends and a passage extending through the ends, and having an opening in the proximal end to receive an inflatable balloon. The balloon generally comprises a substantially flexible, and preferably non-elastic, material having an inflatable space therein, defining a predetermined shape capable of assuming collapsed and inflated conditions.

Inherent with these types of balloon distractors, is that the surface which needs to be observed or worked on is often covered by the balloon material. Inherent in arthroscopic surgeries is a need to access Joint surfaces. As such, what is needed then is a joint distractor that does not suffer from the above-mentioned disadvantages. This, in turn, will provide a substantially conforming joint distractor between the articular cartilage areas, allow for visualization of the articular cartilage areas, and allow for debridement, joint flushing, and smoothing of the joint surfaces.

SUMMARY OF THE INVENTION

In accordance with the teachings of the present invention, a segmented joint distractor for use in the surgical distraction of a joint is disclosed. The segmented joint distractor provides the necessary force and contact surface on the articular cartilage areas to separate the joint while also providing sufficient access to the joint to perform arthroscopic surgical procedures.

In one preferred embodiment, the segmented joint distractor includes a series of fluidly filled spheroids. Disposed between the spheroids is a generally non-expandable pipe region, which allows access to the intra-ariticular area and fluidly couples the spheroids.

In yet another preferred embodiment, a joint distractor having a sequence of circular disks that start flat and increase in thickness is disclosed. Further, a method of distracting the joint by pulling the sequence through a joint to steadily increase the thickness and, hence, the amount of distraction is disclosed.

In yet another preferred embodiment, a joint distractor for separating the intra-articular areas includes a string of varying diameter beads. The string of beads has a series of increasing diameter spheroids strung onto a cord member. The method of distracting a joint is disclosed. The beaded cord is inserted into the joint and pulled through, steadily separating the articular cartilage areas.

Use of the present invention provides a segmented joint distractor with spherical members. The joint distractor provides a substantially full contact surface area on each of the generally spherical members. Between the spherical members, access can be gained to the articular cartilage areas of the joint. As a result, the aforementioned disadvantages associated with the currently available joint distractors have been substantially reduced or eliminated.

BRIEF DESCRIPTION OF THE DRAWINGS

Still other advantages of the present invention will become apparent to those skilled in the art after reading the following specification and by reference to the drawings in which:

FIG. 4 is a view of a second preferred embodiment of the present invention;

FIG. 5 is a side view of a second preferred embodiment of the present invention;

FIG. 9 is a view of a sixth preferred embodiment of the present invention;

FIG. 10 is a view of a seventh preferred embodiment of the present invention;

FIG. 11 is a side view of the embodiment shown in FIG. 10; and

DETAILED DESCRIPTION OF THE PREFERRED EMBODIMENTS

The following description of the preferred embodiments concerning a joint distraction apparatus are merely exemplary in nature and not intended to limit the invention or its application or uses. Moreover, while the present invention is described in detail with respect to a hip joint, it will be appreciated by those skilled in the art that the present invention is clearly not limited to use in distracting a hip joint and may be applied to various other types of joints or body structures, as further discussed herein.

Figure 1:
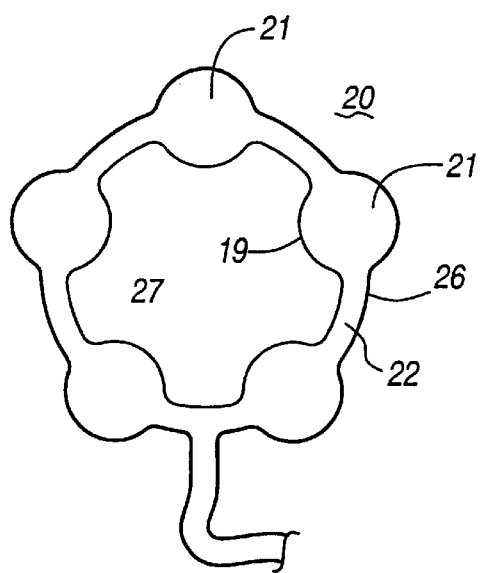
FIG. 1 discloses a top view of the compartmentalized joint distractor according to the teachings of a first preferred embodiment of the present invention.
Figure 2:
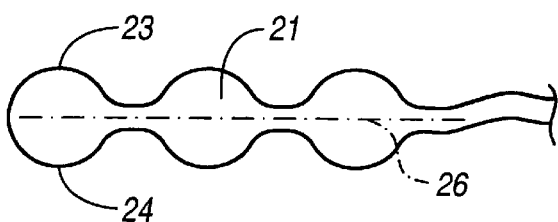
FIG. 2 is a side view of the compartmentalized joint distractor as shown in FIG. 1.

Referring to FIGS. 1 and 2, there is shown a joint distractor 20 according to the teachings of the first preferred embodiment of the present invention. The joint distractor 20 is composed of a pair of generally planar non-elastic members 23 and 24. These polymer members 23 and 24 are coupled together along the inside 19 and outside edges 26 to form a hollow toroid. Formed on the toroid is the series of hollow fluidly coupled generally spheroid members 21. Each of the fluid containing bodies 21 is joined by the tube regions 22. Prior to inflation, the distractor 20 is flat and the planar members 23 and 24 lie in contact with each other.

The fluid in the fluid containing bodies 21 functions to apply pressure to the generally planar elastic or non-elastic members 23 and 24. The members 23 and 24 then in turn apply forces to the articulating surfaces 25 of the joint to separate them. This force is in direct opposition to the forces generated by the ligaments of the joint.

The inside edge 19 of the distractor defines a generally circular area 27 that generates the exposed joint surface 25. These exposed surfaces can then be accessed by the many orthopedic instruments which can enter the generally circular area 27 by passing adjacent the tube regions 22.

Figure 3:
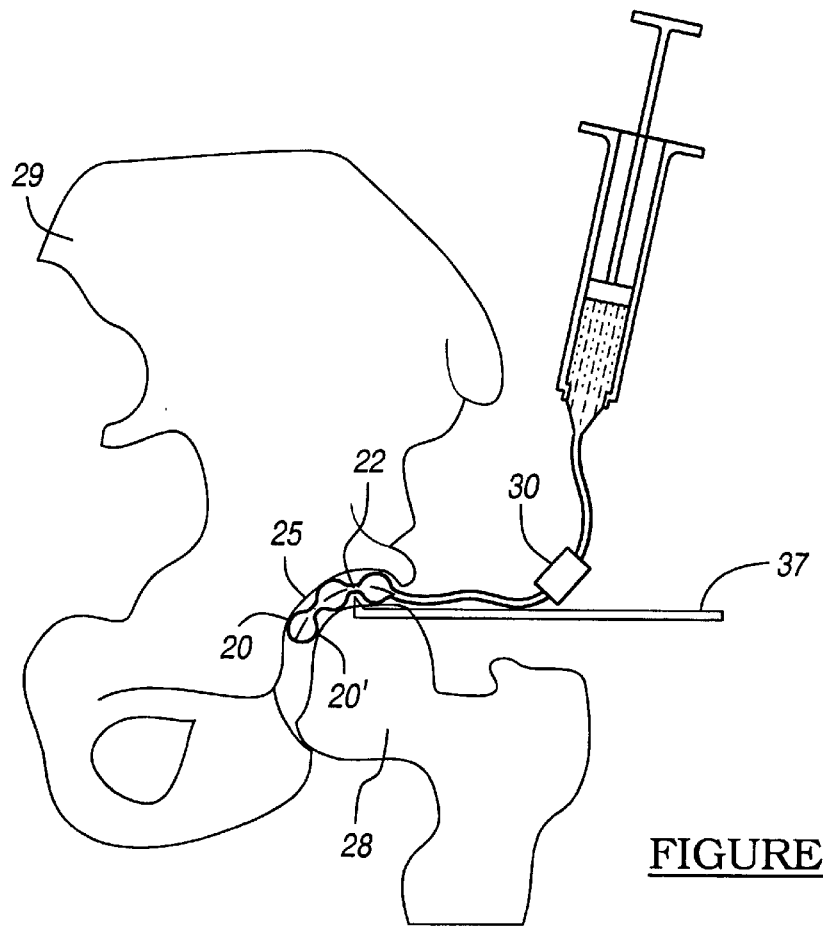
FIG. 3 is a view of the compartmentalized joint distractor of FIGS. 1 and 2 shown disposed within a hip joint.

As shown in FIG. 3, uninflated distractor 20' is positioned adjacent to the surfaces to be separated by insertion through a small incision. The femoral component 28 of the hip joint is partially distracted from the pelvis 29 only enough to position the uninflated distractor 20' between the joint surfaces 25. After insertion between the joint surfaces 25, sterile fluid is injected under pressure by a pressurized fluid source such as a syringe into the sealed distractor 20, filling the generally spheroid members 21.

Once the pressurized fluid fills the generally spheroid members 21, access to the articular cartilage surfaces 25 of the joint is available in the circular region 27, by passing the orthopedic instruments between the inflated spheroids 21 via an appropriate incision. As best seen in FIG. 3, orthopedic instruments 37 can access the articular surface 25 adjacent to the tube region 22. Each fluid distractor 20 preferably includes a valve 30 that regulates the fluid in and out of the spheroids 21. The valve 30 functions to allow fluid into the distractor 20 while it is being pressurized. The sterile fluid can be removed from the distractor 20 by puncturing the surface 23 of the distractor or by releasing fluid through the valve 30.

FIGS. 4 and 5 represent views of a second preferred embodiment of the present invention. Shown is the toroidal joint distractor 31 which is formed by a pair of generally crescent shaped fluid filled spheroids 32 and 33. Coupling the crescent shaped spheroids 32 and 33 are a pair of adjoining fluidly filled tube regions 22. Although the toroidal distractor 31 has fewer tube regions 22 to insert orthopedic instruments 37, the crescent shaped spheroids 32 and 33 provide a larger surface area which impart force on the articular surface 25. The polymer members 23 and 24 forming the crescent shaped spheroids 27 and 28 can be coupled so as to form an angled wedge structure should a particular use call for one.

Figure 6:
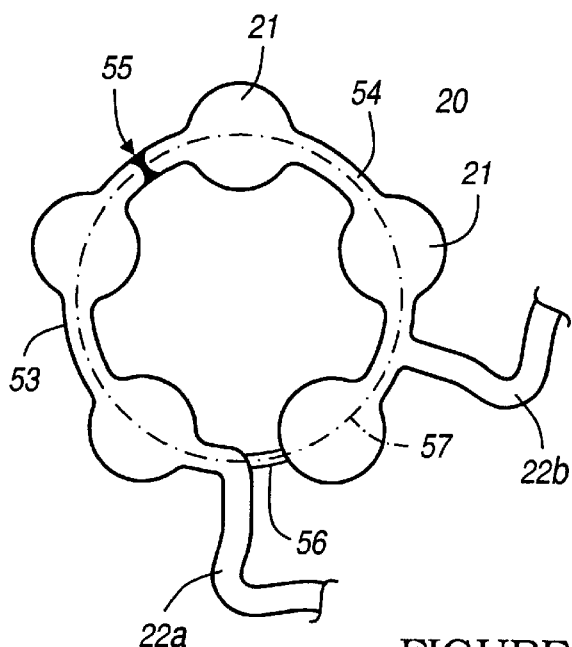
FIG. 6 is a view of a third preferred embodiment of the present invention.

With reference to FIG. 6, there is shown a joint distractor 20 according to the teachings of the third preferred embodiment of the present invention. The joint distractor 20 is composed of two fluidly isolated chambers 53 and 54. These chambers 53 and 54 are each formed by at least one generally spheroid member 21. Each of the chambers 53 and 54 are capable of being filled by separate fluid sources through the tube regions 22a and 22b. Additionally, the separate regions are non-fluidly coupled at regions 55 and 56. As is depicted in FIG. 6, any of the distractors of the current invention can have radio opaque materials 57 such as the wire shown in FIG. 6. These radio opaque materials 57 can take the form of particulate incorporated within the distractor devices 20. When placed within a joint the joint distractor as depicted in FIG. 6 can be used to vary the angle of the joint by increasing or decreasing the amount of fluids in the chambers 53 and 54. By modifying the amount of fluid within the chamber, access to the joint can be obtained adjacent to tube regions 22.

Figure 7:
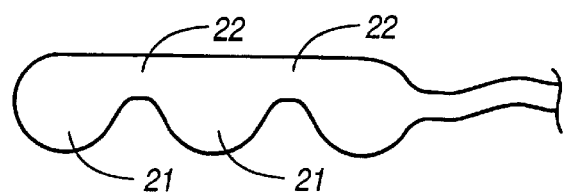
FIG. 7 is a view of a fourth preferred embodiment of the present invention.
Figure 8:
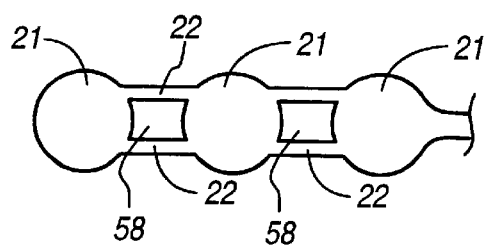
FIG. 8 is a view of a fifth preferred embodiment of the present invention.

FIGS. 7 and 8 show side views of the fourth and fifth embodiments of the present invention. Shown in FIG. 7 is the connected tube region 22 disposed on the top surface of the distractor. This allows for access of the joint area under the tube region 22 and the spaces defined. FIG. 8 shows a plurality of generally spheroidal members 21 coupled by tube members 22 located on the top and bottom surface of the joint distractor. The tube members define openings 58 between the tube members and the generally spheroidal bodies 21. Access to the joint surfaces by medical instruments can be obtained adjacent the tube regions 22.

Figure 12:
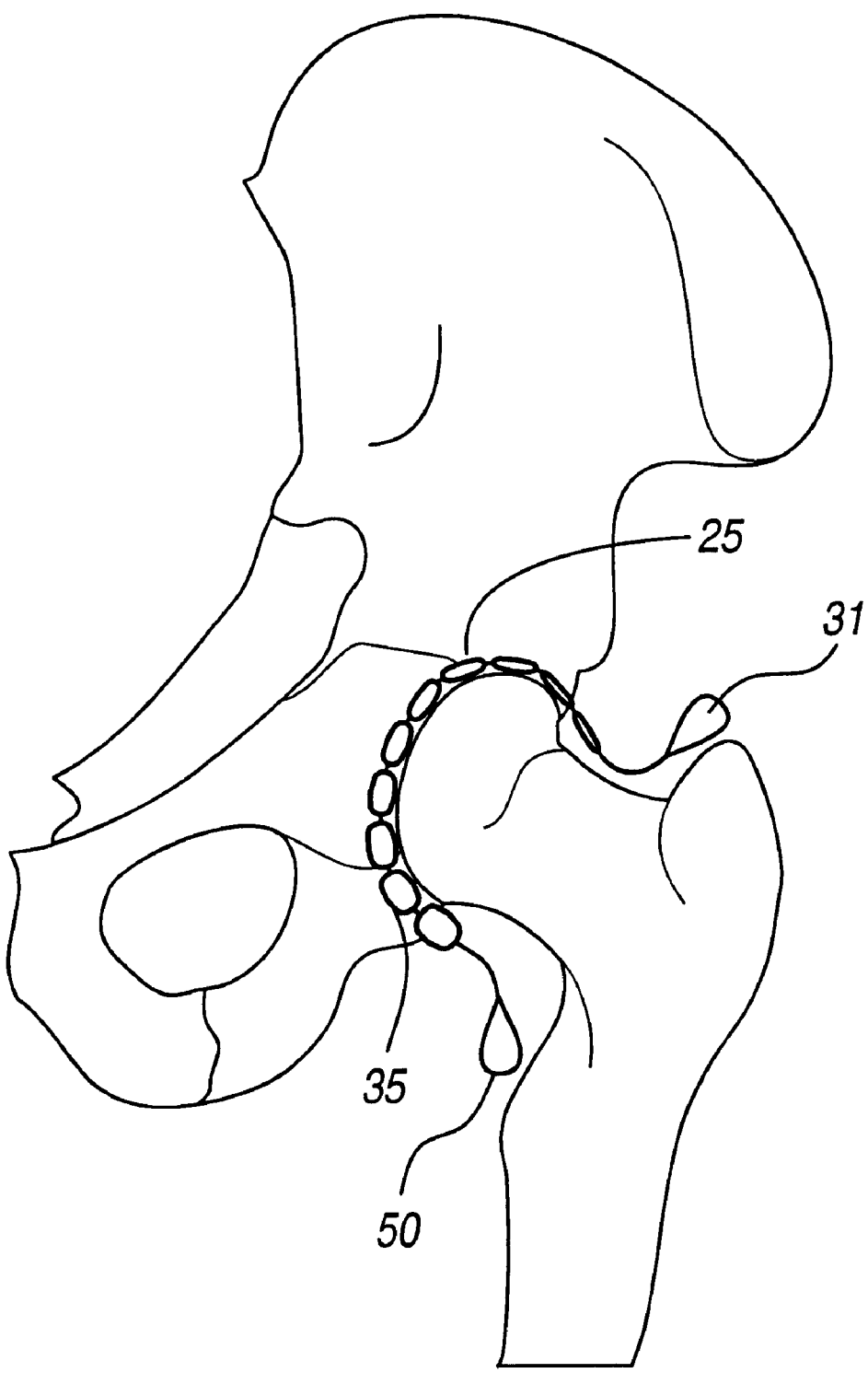
FIG. 12 is a view of the compartmentalized joint distractor of FIG. 10 distracting a joint.

With reference to FIG. 9, a sixth preferred embodiment of the present invention is disclosed. Shown is a distractor 36 having a series of generally spherical elements 38 on a cord 40 having handle elements 50. The string of spherical elements 36, which is pulled through a joint region, functions to separate and hold the joint articular cartilage surfaces 25 apart. The joint is first distracted slightly to separate the surfaces enough to allow passage of the distractor's cord 40. The cord 40 is then pulled through the region from smallest diameter spherical element 42 to a point along the distractor that there is sufficient access space created (see FIG. 12). Access to the joint can be obtained by the use of instruments placed in regions between the spherical elements 38. The spherical elements 38 can be used to hold the surfaces apart after the joint has been distracted by applying forces to separate the members. It is envisioned that the spherical elements 38 be solid or fluid filled.

The series of adjacent spheres 38 are mounted onto a cord or articulating member 40, which is made of fibers or wire by being integrally molded thereon. The spherical elements 38 have an increasing diameter from about 2 mm to about 10 mm, each spherical element 38 increasing in size by about 0.2 mm. The spherical elements 38 can be adjacent one another or can be spaced apart, leaving room between for access by orthopedic instruments 37.

In another embodiment of the current invention, shown in FIG. 10 is a top view of a segmented distractor 46 according to the teachings of a fourth preferred embodiment of the present invention. As can be seen, the distractor 46 has a series of generally circular distractor components 48, each having the same diameter. Also shown are the handle members 50 which are used to pull the through the joint. FIG. 11 shows a side view of the distractor 46 as shown in FIG. 10. As can be seen, the circular distractor components 48 have varying thickness'. The thickness of the distractor components 48 increase from about 2 mm to about 10 mm. Each of these segments has a pair of generally parallel planar regions 51 and 52 with each adjoining distractor component 48 defining a slightly larger thickness. The planar regions optionally can have a slightly angled surface to assist in the facilitation of the separation of the joint.

A wide variety of features can be utilized in the various material disclosed and described above. The foregoing discussion discloses and describes the preferred embodiments of the present invention. One skilled in the art will readily recognize from such discussion, and from the accompanying drawings that various changes, modifications, and variations can be made therein without departing from the true spirit and fair scope of the invention.

What is claimed is:

1. A joint distraction device for facilitating distraction between a first bone and a second bone of a joint during joint arthroscopy, said joint distraction device comprising:
   a first bone engaging surface engageable with the first bone of a patient;
   a second bone engaging surface engageable with the second bone of the patient; and
   the first and second bone engaging surfaces form a plurality of spheroids, wherein upon applying pressure to the spheroids, the spheroids expand so that the first bone engaging surface engages the first bone and the second bone engaging surface engages the second bone to distract the joint between the first bone and the second bone.

2. The joint distraction device according to claim 1 further comprising a plurality of tubular members disposed between said spheroids, the tubular members fluidly coupling the spheroids.

3. The joint distraction device according to claim 2 wherein at least one spheroid has a first radius and said tubular member has a second radius less then said first radius.

4. A joint distraction device for facilitating joint arthroscopy comprising:
   a first engaging surface engageable with a first joint surface of a patient;
   a second engaging surface engageable with a second joint surface of the patient;
   the first and second engaging surfaces form a plurality of spheroids; and
   a fluid injector for inserting pressurized fluid in the spheroids, said fluid injector includes a valve for regulating the amount of fluid in the spheroids.

5. A joint distraction device for facilitating joint arthroscopy comprising:
   a first engaging surface engageable with a first joint surface of a patient;
   a second engaging surface engageable with a second joint surface of the patient; and
   the first and second engaging surfaces form a plurality of spheroids, wherein said spheroids are fluidly coupled together, and are disposed about a common axis to form a circle.

6. A joint distraction device for facilitating distraction between a first bone and a second bone of a joint during joint arthroscopy, said joint distraction device comprising:
   a plurality of expandable members having a first bone engaging surface and a second bone engaging surface operable to engage the first bone and the second bone and operable to distract the joint; and
   a plurality of delivery tubes in communication with said plurality of expandable members, said plurality of delivery tubes operable to deliver fluid to said plurality of expandable members, wherein upon delivery of the fluid, said plurality of expandable members expand where the first bone engaging surface and the second bone engaging surface engage the first bone and the second bone to distract the joint.

7. The joint distraction device as defined in claim 6 wherein said plurality of delivery tubes defines a plurality of access areas to gain access to the distracted joint.

8. The joint distraction device as defined in claim 6 further comprising radio opaque materials.

9. The joint distraction device as defined in claim 6 comprising a plurality of fluid sources.

10. The joint distraction device of claim 6 wherein the plurality of delivery tubes define at least one joint access orifice.

11. A joint distraction device for facilitating joint arthroscopy, said joint distraction device comprising:
    a plurality of expandable members operable to distract a joint; and
    a plurality of delivery tubes in communication with said plurality of expandable members, said plurality of delivery tubes operable to deliver fluid to said plurality of expandable members, wherein upon delivery of the fluid, said plurality of expandable members distract the joint, and wherein said plurality of expandable members is configured as a toroid.

12. The joint distraction device as defined in claim 11 wherein each of said expandable members is shaped as a sphere.

* * * * *